(12) United States Patent
Akatsuka et al.

(10) Patent No.: US 8,865,208 B2
(45) Date of Patent: Oct. 21, 2014

(54) VESICLE USEFUL FOR EXTERNAL PREPARATION FOR SKIN, AND EXTERNAL PREPARATION FOR SKIN COMPRISING THE VESICLE

(75) Inventors: Hidetaka Akatsuka, Yokohama (JP); Hitoshi Imamura, Yokohama (JP); Yasuyuki Ishihara, Yokohama (JP)

(73) Assignee: Pola Chemical Industries Inc., Shizuoka (JP)

( * ) Notice: Subject to any disclaimer, the term of this patent is extended or adjusted under 35 U.S.C. 154(b) by 1019 days.

(21) Appl. No.: 12/601,481

(22) PCT Filed: Apr. 10, 2008

(86) PCT No.: PCT/JP2008/057081
§ 371 (c)(1),
(2), (4) Date: Nov. 23, 2009

(87) PCT Pub. No.: WO2008/149601
PCT Pub. Date: Dec. 11, 2008

(65) Prior Publication Data
US 2010/0172964 A1    Jul. 8, 2010

(30) Foreign Application Priority Data

May 29, 2007  (JP) .................................. 2007-141345

(51) Int. Cl.
| | | |
|---|---|---|
| A61K 9/127 | (2006.01) | |
| A61K 8/44 | (2006.01) | |
| A61K 8/41 | (2006.01) | |
| A61K 8/64 | (2006.01) | |
| A61K 8/34 | (2006.01) | |
| A61K 36/00 | (2006.01) | |
| A61K 8/68 | (2006.01) | |
| A61K 8/63 | (2006.01) | |
| A61K 8/14 | (2006.01) | |
| A61K 31/56 | (2006.01) | |
| A61K 8/60 | (2006.01) | |
| A61Q 19/00 | (2006.01) | |
| A61K 8/97 | (2006.01) | |
| A61K 8/67 | (2006.01) | |
| A61K 31/05 | (2006.01) | |
| A61K 31/352 | (2006.01) | |
| A61K 8/39 | (2006.01) | |
| A61K 31/7048 | (2006.01) | |
| A61K 8/86 | (2006.01) | |
| A61K 8/368 | (2006.01) | |
| A61K 8/37 | (2006.01) | |
| A61K 8/49 | (2006.01) | |
| A61K 31/16 | (2006.01) | |
| A61K 31/164 | (2006.01) | |
| A61K 31/19 | (2006.01) | |
| A61K 9/00 | (2006.01) | |

(52) U.S. Cl.
CPC .................. *A61K 9/0014* (2013.01); *A61K 8/44* (2013.01); *A61K 8/41* (2013.01); *A61K 8/64* (2013.01); *A61K 8/347* (2013.01); *A61K 36/00* (2013.01); *A61K 8/68* (2013.01); *A61K 8/63* (2013.01); *A61K 8/14* (2013.01); *A61K 31/56* (2013.01); *A61K 8/602* (2013.01); *A61Q 19/00* (2013.01); *A61K 8/97* (2013.01); *A61K 8/676* (2013.01); *A61K 8/975* (2013.01); *A61K 31/05* (2013.01); *A61K 31/352* (2013.01); *A61K 8/39* (2013.01); *A61K 31/7048* (2013.01); *A61K 8/86* (2013.01); *A61K 8/368* (2013.01); *A61K 8/375* (2013.01); *A61K 8/498* (2013.01); *A61K 31/16* (2013.01); *A61K 31/164* (2013.01); *A61K 31/19* (2013.01)
USPC ........................................................ 424/450

(58) Field of Classification Search
CPC ........................................................ A61K 9/127
USPC ........................................................ 424/450
See application file for complete search history.

(56) References Cited

U.S. PATENT DOCUMENTS

| | | | | |
|---|---|---|---|---|
| 5,723,146 | A | * | 3/1998 | Rossling et al. ............. 424/450 |
| 5,776,488 | A | * | 7/1998 | Mori et al. .................... 424/450 |
| 6,416,768 | B1 | | 7/2002 | Ravaux et al. |
| 8,182,835 | B2 | * | 5/2012 | Kim et al. ..................... 424/450 |
| 2006/0029657 | A1 | * | 2/2006 | Popp et al. .................... 424/450 |

FOREIGN PATENT DOCUMENTS

| | | |
|---|---|---|
| EP | 1 027 878 | 8/2000 |
| EP | 1 891 924 | 2/2008 |
| FR | 2730931 | 8/1996 |
| JP | 59 148745 | * 8/1984 |
| JP | 09-040543 | 2/1997 |
| JP | 09-143050 | 6/1997 |
| JP | 09-169637 | 6/1997 |
| JP | 10-265379 | 10/1998 |
| JP | 11-335271 | 12/1999 |

(Continued)

*Primary Examiner* — Gollamudi Kishore
(74) *Attorney, Agent, or Firm* — Knobbe, Martens, Olson & Bear LLP

(57) ABSTRACT

Disclosed is a technique for allowing an active ingredient as an agent for improving or maintaining the dermal environment to reach a dermis. Specifically disclosed is a vesicle comprising the following components 1) to 3): 1) an α,ε-bis(γ-N—($C_{10-30}$)acylglutamyl)lysine and/or a salt thereof; 2) ceramide and/or a derivative thereof; and 3) one or more selected from a glycerin fatty acid ester, a polyglycerin fatty acid ester and a pyroglutamic acid glycerin fatty acid ester. The acyl group in the α,ε-bis(γ-N—($C_{10-30}$)acylglutamyl)lysine is preferably a lauroyl group. The ceramide or the derivative thereof is preferably ceramide type-2 or ceramide type-3. The vesicle can encapsulate an active ingredient. The vesicle can be contained in an external preparation for the skin.

11 Claims, No Drawings

(56) References Cited

FOREIGN PATENT DOCUMENTS

| | | |
|---|---|---|
| JP | 2000-103722 | 4/2000 |
| JP | 2000-344653 | 12/2000 |
| JP | 2002-029988 | 1/2002 |
| JP | 2003-113027 | 4/2003 |
| JP | 2004-143080 | 5/2004 |
| JP | 2004-182687 | 7/2004 |
| JP | 2004-250354 | 9/2004 |
| JP | 2005-035911 | 2/2005 |
| JP | 2005-132823 | 5/2005 |
| JP | 206-160650 | 6/2006 |
| JP | 2006-160650 | 6/2006 |
| JP | 2006-199634 | 8/2006 |
| JP | 2006-199635 | 8/2006 |
| JP | 2006-225373 | 8/2006 |
| JP | 2006-290894 | 10/2006 |
| JP | 2007-332088 | 12/2007 |
| JP | 2007-332089 | 12/2007 |
| JP | 2008-019230 | 1/2008 |
| WO | WO 2006/134890 | 12/2006 |

* cited by examiner

VESICLE USEFUL FOR EXTERNAL PREPARATION FOR SKIN, AND EXTERNAL PREPARATION FOR SKIN COMPRISING THE VESICLE

CROSS-REFERENCE TO RELATED APPLICATIONS

This application is the U.S. National Phase under 35 U.S.C. §371 of International Application PCT/JP2008/057081, filed Apr. 10, 2008, which was published in a non-English language, which claims priority to JP Patent Application No. 2007-141345, filed May 29, 2007.

TECHNICAL FIELD

The present invention relates to a formulation technique useful for an external preparation for skin, and more specifically, to a formulation technique utilizing a vesicle. The present invention also relates to an external preparation for skin utilizing the formulation technique.

BACKGROUND ART

Skin is an important tissue for separating a living body and an outside world. Accordingly, if the skin suffers disorder, it means that the protective barrier of the living body collapses, and the disorder may cause serious damage to the living body. In this context, disorders such as damage on the skin need to be eliminated rapidly. However, a protective barrier function of the skin becomes a hindrance for allowing a drug for eliminating the disorder to reach the skin, especially to the dermis, and hence there was a condition that smooth elimination of the disorder hardly occurs. Accordingly, there is a need to develop a technique to accurately deliver a drug to be delivered to the dermis.

Under the above-mentioned condition as a background, there have been attempted various developments on means for promoting percutaneous absorption. For example, there are exemplified: a method involving utilizing a card-house or net-work structure formed by an oil-based gel (Patent Document 1); a method involving utilizing an ultrasonic wave as a driving force for percutaneous absorption (Patent Document 2); a method involving utilizing a solvent such as N-methyl-2-pyrrolidone (Patent Document 3); a method involving utilizing a percutaneous absorption promoting ingredient such as lauroyl sarcosine (Patent Document 4); and a method involving allowing a liposome or a niosome, which is a sphere having a phospholipid bilayer structure including an aqueous core, to encapsulate a drug into the aqueous core and blending the resultant to an external preparation for skin (Patent Document 5). Those technologies enabled improvements in reaching degree of a drug to the dermis, but the reaching degree was far from sufficient, and in considerable cases, the above-mentioned means for promoting percutaneous absorption impaired the defense function of the skin itself.

On the other hand, as a formulation technique utilizing a vesicle, there are known techniques in which insoluble ingredients such as a ceramide and phytosterol are stably blended in an external preparation for skin (Patent Document 6 and Patent Document 7). Further, there is also known a technique in which an ingredient that is reactive with water is encapsulated into a vesicle to stably contain the vesicle into a water-based formulation (Patent Document 8). However, in those vesicle techniques, a surfactant for forming the vesicle is a cationic surfactant. Accordingly, its application other than to washing material is difficult, and there were many cases in which the stability of the vesicle itself was problematic. As a result, it is difficult to apply the vesicle to an external preparation for skin which is not capable of being washed off.

On the other hand, a vesicle, which contains an $\alpha,\epsilon$-bis($\epsilon$-N—($C_{10-30}$)acylglutamyl)lysine and/or a salt thereof, is completely unknown.

It should be noted that, an extract of *Coptis* (Ranunculaceae), an extract of *Citrus aurantium* (Rutaceae), an extract of red algae, and an extract of *Houttuynia* (Saururaceae) each have a function of adjusting the calcium ion concentration gradient of the epidermis to reinforce the skin barrier function (Patent Document 9). It is known that an extract of *Rosmarinus officinalis* has a function of suppressing decomposition of elastin (Patent Document 10). It is known that an extract of *Betula alba* has a function of suppressing a Maillard reaction (Patent Document 11). It is known that extracts of *Achillea* and *Ophiopogon* each have a function of suppressing extension of dendrite in melanocyte (Patent Document 12 and Patent Document 13). It is known that an extract of *Syzygium aromaticum*, and triterpenes such as oleanolic acid, betulinic acid, and betuline each have a function to restore dermis collagen fiber bundle (Patent Document 14 and Patent Document 15). It is known that a natural protein hydrolysate has a function to inhibit elastase (Patent Document 16). It is known that pantetheine sulfonate or a derivative thereof and glycyrrhetinic acid or a derivative thereof each have a function of suppressing an inflammatory factor. It is known that hydroquinone or a glycoside thereof, esculin, esculetin, glabridin, methoxysalicylic acid, tranexamic acid or a derivative thereof, and ascorbic acid or a derivative thereof each have a function of eliminating active oxygen to prevent oxidation stress from being applied onto the dermis (Patent Document 17).

[Patent Document 1] JP 2000-103722 A
[Patent Document 2] JP H11-335271 A
[Patent Document 3] JP H10-265379 A
[Patent Document 4] JP H09-169637 A
[Patent Document 5] JP 2004-143080 A
[Patent Document 6] JP 2006-199635 A
[Patent Document 7] JP 2006-199634 A
[Patent Document 8] JP H09-40543 A
[Patent Document 9] JP 2006-331294 A
[Patent Document 10] JP 2005-132823 A
[Patent Document 11] JP 2005-35911 A
[Patent Document 12] JP 2003-113027 A
[Patent Document 13] JP 2004-250354 A
[Patent Document 14] JP 2002-29988 A
[Patent Document 15] JP H09-143050 A
[Patent Document 16] JP 2004-182687 A
[Patent Document 17] JP 2000-344653 A

DISCLOSURE OF THE INVENTION

The present invention has been achieved in view of the above-mentioned circumstances, and an object of the present invention is to provide a technique for allowing an active ingredient for improving or maintaining a dermal environment to reach the dermis.

In view of the above-mentioned circumstances, the inventors of the present invention have intensively studied on the technique for allowing an active ingredient for improving or maintaining a dermal environment to reach the dermis, and as a result, they have found that the following vesicle has high dermis-reaching property and excellent encapsulating property of an active ingredient, and in addition, a function of adjusting the dermal environment in the vesicle itself, the vesicle comprising: 1) an $\alpha,\epsilon$-bis($\gamma$-N—($C_{10-30}$)acylglutamyl)lysine and/or a salt thereof, 2) a ceramide and/or a derivative thereof, and 3) one or more selected from a glycerin fatty acid ester, a polyglycerin fatty acid ester, and a pyroglutamic acid glycerin fatty acid ester. Thus, the present invention has been accomplished. That is, the present invention is as follows.

(1) A vesicle comprising:
1) an $\alpha,\epsilon$-bis($\gamma$-N—($C_{10-30}$)acylglutamyl)lysine and/or a salt thereof;
2) a ceramide and/or a derivative thereof; and
3) one or more selected from a glycerin fatty acid ester, a polyglycerin fatty acid ester, and a pyroglutamic acid glycerin fatty acid ester.

(2) A vesicle according to item (1), wherein an acyl group in the $\alpha,\epsilon$-bis($\gamma$-N—($C_{10-30}$)acylglutamyl)lysine is a lauroyl group.

(3) A vesicle according to item (1) or (2), wherein the ceramide or the derivative thereof is a ceramide type 2 or a ceramide type 3.

(4) A vesicle according to any one of items (1) to (3), wherein the one or more selected from a glycerin fatty acid ester, a polyglycerin fatty acid ester, and a pyroglutamic acid glycerin fatty acid ester are one or more selected from diglycerin monooleate, diglycerin monoisostearate, decaglycerin monooleate, decaglycerin monoisostearate, decaglycerin pentaoleate, and decaglycerin pentaisostearate.

(5) A vesicle according to any one of items (1) to (4), further comprising one or more of the following active ingredients for improving or maintaining a dermal environment: an extract of *Coptis* (Ranunculaceae); an extract of *Citrus aurantium* (Rutaceae); an extract of red algae; an extract of *Houttuynia* (Saururaceae); an extract of *Rosmarinus officinalis* (Lamiaceae); an extract of *Betula alba* (Betulaceae); an extract of *Achillea* (Asteraceae); an extract of *Syzygium aromaticum* (Myrtaceae); an extract of *Hypericum* (Guttiferae); an extract of *Centella* of (Umbelliferae); an extract of *Engelhardtia chrysolepis* (Juglandaceae); an extract of *Ophiopogon* (Liliaceae); a natural protein hydrolysate or an acylated product thereof; oleanolic acid or a derivative thereof; betuline; betulinic acid or a derivative thereof; pantetheine sulfonate or a derivative thereof; glycyrrhetinic acid or a derivative thereof; hydroquinone or a glycoside thereof; esculin; esculetin; glabridin; methoxysalicylic acid; tranexamic acid or a derivative thereof; ascorbic acid or a derivative thereof; and L-carnitine.

(6) An external preparation for skin, comprising the vesicle according to any one of items (1) to (5).

BEST MODE FOR CARRYING OUT THE INVENTION (1) $\alpha,\epsilon$-bis($\gamma$-N—($C_{10-30}$)Acylglutamyl)Lysine which is Essential Ingredient of Vesicle of the Present Invention An external preparation for skin of the present invention contains an $\alpha,\epsilon$-bis($\gamma$-N—($C_{10-30}$)acylglutamyl)lysine as an essential ingredient. The $\alpha,\epsilon$-bis($\gamma$-N—($C_{10-30}$)acylglutamyl)lysine may also be contained in a form of a free body or a salt. The salt thereof may be used without any limitation as long as the salt is one which may be used for an external preparation for skin. For example, favorable examples thereof include: alkali metal salts such as a sodium salt and a potassium salt; alkaline earth metal salts such as a calcium salt and a magnesium salt; organic amine salts such as an ammonium salt, a triethylamine salt, triethanolamine salt, and a monoethanolamine salt; and basic amino-acid salts such as a lysine salt and an alginic acid salt. The acyl group is characterized by including 10 to 30 carbon atoms. The acyl group may be linear, branched, or cyclic, and may be a saturated aliphatic group or an unsaturated aliphatic group. Specific examples of the acyl group include a decanoyl group, a lauroyl group, a myristoyl group, a palmitoyl group, a stearoyl group, a behenoyl group, an isostearoyl group, an oleoyl group, and a linoleoyl group. Of those, the lauroyl group is particularly preferred. Further, the $\alpha,\epsilon$-bis($\gamma$-N—($C_{10-30}$)acylglutamyl)lysine contains two acyl groups, and the two acyl groups may be the same as or different from each other. The $\alpha,\epsilon$-bis ($\gamma$-N—($C_{10-30}$)acylglutamyl)lysine may be produced by, for example, the following procedure. That is, the procedure includes reacting glutamic acid with acyl chloride in the presence of alkali such as triethylamine to thereby obtain N-acylglutamic acid, and then condensing N-acylglutamic acid in the presence of lysine and a peptide synthesis reagent such as DCC at a 2:1 molar ratio. The thus obtained reaction product may be purified with a silica gel column chromatography or the like. As an elution solvent of the silica gel column chromatography, there may be preferably exemplified a chloroform-methanol mixed solution type. The structure of the $\alpha,\epsilon$-bis($\gamma$-N—($C_{10-30}$)acylglutamyl)lysine is shown in Formula 1.

[Chem 1]

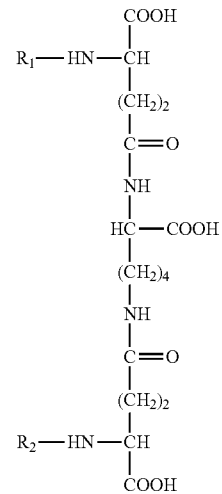

Formula 1 (but, in the formula, $R_1$ and $R_2$ each independently represent an acyl group having 10 to 30 carbon atoms.)

The $\alpha,\epsilon$-bis($\gamma$-N—($C_{10-30}$)acylglutamyl)lysine may be produced according to the above-mentioned method and used. However, there already exists commercially-available $\alpha,\epsilon$-bis($\gamma$-N—($C_{10-30}$)acylglutamyl)lysine, and the commercially-available product may be purchased and used. As the commercially-available product described above, there may be preferably exemplified "Pellicer L-30" (manufactured by Asahi Kasei Corporation; $\alpha,\epsilon$-bis ($\gamma$-N-lauroylglutamyl) lysine). The thus obtained $\alpha,\epsilon$-bis($\gamma$-N—($C_{10-30}$)acylglutamyl)lysine has a property with which a bilayer membrane is easily formed, and, by this function, forms a vesicle having an excellent stability with other essential ingredients described later. The vesicle has physical properties that are approximate to those of the membrane structure of epidermal cells, and hence is excellent in skin permeability. In addition, the vesicle is excellent in the function of retaining an active ingredient between lipid bilayer membranes. This owes to an amphipathic property of the lipid bilayer membranes themselves. Further, in order to exhibit such function, the vesicle contains one or more selected from the α,ε-bis(γ-N—($C_{10-30}$)acylglutamyl)lysine in a total amount of, with respect to the total amount of the vesicle, preferably 1 mass % or more preferably 5 mass % as a lower limit, and preferably 50 mass %, or more preferably 10 mass % as an upper limit. This is because that there are cases where the stable vesicle may not be formed even if the amount of the above-mentioned ingredients is too large or too small.

(2) Ceramide and Derivative Thereof, which are Essential Ingredients of Vesicle of the Present Invention The vesicle of the present invention is characterized by containing a ceramide and a derivative thereof (herein, sometime collectively referred to as "ceramides"). It is known that there are generally seven types of ceramides including type 1 to type 7 (represented by the following formulae 2 to 7), and anyone of those may be used. Of those, type 2 is particularly preferred, and N-stearoyldihydroxysphingosine is particularly preferred. Those ceramides are commercially available, and such commercially-available products may be purchased and used. As the commercially-available products, there may be preferably exemplified: "Ceramide I" (manufactured by Cosmo-Farm) containing N-(27-octadecanoyloxy-heptacosanoyl-)-phytosphingosine, which being type 1 as an ingredient; "Ceramide TIC-001" (manufactured by Takasago International Corporation) containing N-stearoyl-dihydroxysphingosine, which being type 2 as an ingredient; "Ceramide III" (manufactured by Cosmo-Farm) containing N-stearoyl-phytosphingosine, which being type 3 as an ingredient; "Ceramide IIIA" (manufactured by Cosmo-Farm) containing N-linoleoyl-phytosphingosine, which being type 3 as an ingredient; "Ceramide IIIB" (manufactured by Cosmo-Farm) containing N-oleoyl-phytosphingosine, which being type 3 as an ingredient; and "Ceramide VI" (manufactured by Cosmo-Farm) containing N-2-hydroxystearoyl-phytosphingosine, which being type 6 as an ingredient. Those ceramides may be contained singly or in combination of two or more. In the vesicle of the present invention, those ingredients each have a function of reinforcing the vesicle structure formed by the α,ε-bis(γ-N—($C_{10-30}$)acylglutamyl)lysine. In order to exhibit such an effect, the vesicle contains ceramides in an amount of, with respect to the total amount of the vesicle, preferably 1 mass %, or more preferably 5 mass % as a lower limit, and preferably 50 mass %, or more preferably 10 mass % as an upper limit. If the amount of the ingredient is too large, the above-mentioned effect may not be exhibited in some cases. Further, the ratio of the total of the mass the ceramides to the total of the mass the α,ε-bis(γ-N—($C_{10-30}$)acylglutamyl)lysine is preferably 2:1 to 1:50, and more preferably 1:1 to 1:5.

[Chem 2]

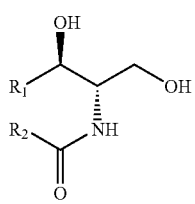

Formula 2

Ceramide Type 1
($R_1$ represents an alkyl group or an alkenyl group, and $R_2$ represents a linoleoyloxyalkyl group. The carbon number of the alkyl group or the alkenyl group represented by $R_1$ is generally in a range of 15 to 18, and the carbon number of the linoleoyloxyalkyl group represented by $R_2$ is generally in the range of 45 to 50.)

Ceramide Type 2
($R_1$ and $R_2$ each independently represent an alkyl group or an alkenyl group. The carbon number of the alkyl group or the alkenyl group represented by $R_1$ or $R_2$ is generally in the range of 15 to 23.)

[Chem 3]

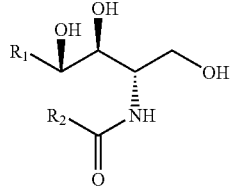

Formula 3

Ceramide Type 3
($R_1$ and $R_2$ each independently represent an alkyl group. The carbon number of the alkyl group represented by $R_1$ or $R_2$ is generally in the range of 15 to 23.)

[Chem 4]

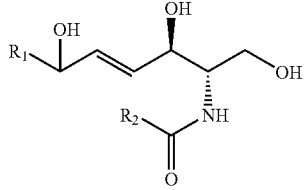

Formula 4

Ceramide Type 4
($R_1$ represents an alkyl group and $R_2$ represents a linoleoyloxyalkyl group. The carbon number of the alkyl group represented by $R_1$ is generally in the range of 15 to 23, and the carbon number of the linoleoyloxyalkyl group represented by $R_2$ is generally in the range of 45 to 50.)

[Chem 5]

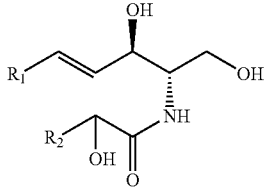

Formula 5

Ceramide Type 5
($R_1$ and $R_2$ each independently represent an alkyl group. The carbon number of the alkyl group represented by $R_1$ or $R_2$ is generally in the range of 15 to 23.)

[Chem 6]

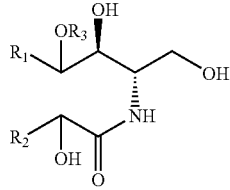

Formula 6

Ceramide Type 6

($R_1$ and $R_2$ each independently represent an alkyl group, and $R_3$ represents a hydrogen atom or an alkyl group. The carbon number of the alkyl group represented by $R_1$ and $R_2$ is generally in the range of 15 to 22.)

[Chem 7]

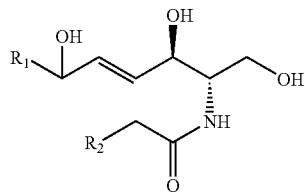

Formula 7

Ceramide Type 7

($R_1$ and $R_2$ each independently represent an alkyl group. The carbon number of the alkyl group represented by $R_1$ or $R_2$ is generally in the range of 15 to 22.)

As ceramide derivatives, ceramide analogues or the like such as sphingosine, sphingomyelin, sphingosylphosphorylcholine, and those described in, for example, JP S62-228048 A, JP S63-216812 A, JP S63-227513 A, JP S64-29347 A, JP S64-31752 A, and JP H8-319263 A are preferably exemplified. Specifically, the ceramide derivatives can be preferably exemplified in the ingredients of the following formula 8 and the ingredients of the following formula 9.

[Chem 8]

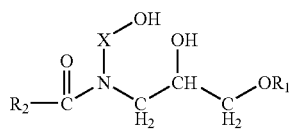

Formula 8

(but, in the formula, $R_1$ represents a hydrocarbon group having 10 to 26 carbon atoms, $R_2$ represents a hydrocarbon group having 9 to 25 carbon atoms, and X represents a group represented by —$(CH_2)_n$— in which n represents 2 to 6.)

[Chem 9]

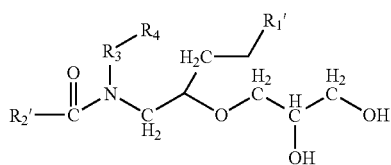

Formula 9

(In the formula, $R_{1'}$ and $R_{2'}$ each independently represent a hydrocarbon group having 1 to 40 carbon atoms, which may be hydroxylated, $R_3$ represents a linear or branched alkylene group having 1 to 6 carbon atoms or a single bond, and $R_4$ represents a hydrogen atom, a linear or branched alkoxy group having 1 to 12 carbon atoms, or a 2,3-dihydroxypropyloxy group. However, $R_4$ represents a hydrogen atom when $R_3$ represents a single bond.)

The ingredient represented by the formula 8 or 9 can be produced by a usual method in accordance with the contexts of the above-mentioned patent documents.

(3) Glycerin Fatty Acid Ester, Polyglycerin Fatty Acid Ester, and Pyroglutamic Acid Glycerin Fatty Acid Ester, which are Essential Ingredients of Vesicle of the Present Invention The vesicle of the present invention contains as essential ingredients one or more of the ingredients chosen from a polyglycerin fatty acid ester and a pyroglutamic acid glycerin fatty acid ester.

Preferred examples of the fatty acid residues of the glycerin fatty acid ester include a lauric acid residue, amyristic acid residue, a palmitic acid residue, a stearic acid residue, a behenic acid residue, an isostearic acid residue, an oleic acid residue, a linolic acid residue, and a linoleic acid residue, and the oleic acid residue, the stearic acid residue, and the isostearic acid residue are particularly preferred.

Further, the degree of polymerization of glycerin in the polyglycerin of polyglycerin fatty acid ester is preferably 2 to 20, and more preferably 2 to 10. Further, preferred examples of the fatty acid residues include a lauric acid residue, a myristic acid residue, a palmitic acid residue, a stearic acid residue, behenic acid residue, an isostearic acid residue, an oleic acid residue, a linolic acid residue, and a linoleic acid residue, and the oleic acid residue, the stearic acid residue, and the isostearic acid residue are particularly preferred. In the polyglycerin fatty acid ester described above, it is preferred that the number of fatty acid residues per molecule be more than the number of free hydroxyl groups. Exemplifying specific examples, a diglycerin monooleic acid ester, a diglycerin monolauric acid ester, a diglycerin monostearic acid ester, a diglycerin monoisostearic acid ester, a triglycerin dilauric acid ester, a triglycerin distearic acid ester, a triglycerin dioleic acid ester, a triglycerin diisostearic acid ester, a pentaglycerin trilauric acid ester, a pentaglycerin tristearic acid ester, a pentaglycerin trioleic acid ester, a pentaglycerin triisostearic acid ester, a heptaglycerin tetralauric acid ester, a heptaglycerin tetrastearic acid ester, a heptaglycerin tetraoleic acid ester, a heptaglycerin tetraisostearic acid ester, a decaglycerin pentalauric acid ester, a decaglycerin pentastearic acid ester, a decaglycerin pentaoleic acid ester, and a decaglycerin pentaisostearic acid ester are particularly preferably exemplified. As a matter of course, those having higher numbers of hydroxyl groups such as a decaglycerin monolauric acid ester, a decaglycerin monostearic acid ester, a decaglycerin monoisostearic acid ester, and a decaglycerin monooleic acid ester exhibit the effect, and, therefore, may also be used.

Examples of ingredients which have the same effect as the polyglycerin fatty acid ester include pyroglutamic acid glycerin fatty acid esters such as a pyroglutamic acid glycerin stearic acid ester and a pyroglutamic acid glycerin oleic acid ester. Those ingredients may be used in the vesicle of the present invention.

The above-mentioned ceramides and $\alpha,\epsilon$-bis($\gamma$-N—($C_{10-30}$)acylglutamyl)lysine can form a stable vesicle only in the presence of the above-mentioned one or more selected from a glycerin fatty acid ester, a polyglycerin fatty acid ester, and a pyroglutamic acid glycerin fatty acid ester. In order to form the stable vesicle, it is preferred that one or more selected from the glycerin fatty acid ester, the polyglycerin fatty acid ester, and the pyroglutamic acid glycerin fatty acid ester be contained in a total amount of, with respect to the total amount of the vesicle, preferably 5 to 30 mass % and more preferably 10 to 25 mass %. Further, the ratio of the total of the mass of the glycerin fatty acid ester, the polyglycerin fatty acid ester, and the pyroglutamic acid glycerin fatty acid ester to the total of the mass of the $\alpha,\epsilon$-bis($\gamma$-N—($C_{10-30}$)acylglutamyl)lysine is preferably 5:1 to 1:1, and more preferably 4:1 to 2:1. The interaction between the two members adjusts the alignment of the lipid bilayer membrane. The thus adjusted bilayer membranes may retain an active ingredient therebetween. Further, there is compatibility between the outer wall of the bilayer membrane vesicle and the cell layer of a horny layer, and hence, the vesicle has excellent horny layer permeability. Further, both the ceramides and the $\alpha,\epsilon$-bis($\gamma$-N—($C_{10-30}$)acylglutamyl)lysine each exhibit a preferred function with respect to the dermis, and hence, even the vesicle which does not contain the above-mentioned active ingredient exhibits an excellent effect of improving or maintaining the dermal environment.

The vesicle of the present invention may be a vesicle which contains one or more of active ingredients for improving or maintaining a dermal environment depending on its purpose.

The phrase "improving or maintaining a dermal environment" specifically includes the following: to enhance skin barrier function; to suppress decomposition of elastin; to suppress a Maillard reaction or to improve nonuniformity of the Maillard reaction; to suppress extension of dendrite in melanocyte; to restore dermis collagen fiber bundle; to inhibit elastase; to suppress an inflammatory factor; to eliminate active oxygen; and the like.

Specific examples of the above-mentioned active ingredients include, for example, an extract of *Coptis* (Ranunculaceae), an extract of *Citrus aurantium* (Rutaceae), an extract of red algae (Palmaria), an extract of *Houttuynia* (Saururaceae), an extract of *Rosmarinus officinalis* (Lamiaceae), an extract of *Betula* (Betulaceae), an extract of *Achillea* (Asteraceae) such as *Achillea millefolium*, an extract of *Syzygium* (Myrtaceae), an extract of *Hypericum* (Clusiaceae) such as *Hypericumperforatum*, an extract of *Centella* (Apiaceae), an extract of *Engelhardtia chrisolepis* (Juglandaceae), an extract of *Ophiopogon* (Liliaceae), natural protein-hydrolyzed products or acylated compounds thereof such as soybean protein-hydrolyzed products, silk protein-hydrolyzed products, and marine collagen-hydrolyzed products, oleanolic acid and derivatives thereof, betulin, betulinic acid and derivatives thereof, pantethine sulfonic acid and derivatives thereof, glycyrrhetinic acid and derivatives thereof, hydroquinone and glycosides thereof, esculin, esculetin, glabridin, methoxysalicylic acid, tranexamic acid and derivatives thereof, ascorbic acid and derivatives thereof, and L-carnitine.

The extract of *Coptis* (Ranunculaceae), the extract of *Citrus aurantium* (Rutaceae), the extract of red algae, and the extract of *Houttuynia* (Saururaceae) each have a function of adjusting the calcium ion concentration gradient of the epidermis to reinforce the skin barrier function. The extract of *Rosmarinus officinalis* has a function of suppressing decomposition of elastin. The extract of *Betula alba* has a function of suppressing a Maillard reaction or to improve nonuniformity of the Maillard reaction. The extracts of *Achillea* and *Ophiopogon* each have a function of suppressing extension of dendrite in melanocyte. The extract of *Syzygium aromaticum*, eugenol, and triterpenes such as oleanolic acid, betulinic acid, and betuline each have a function to restore dermis collagen fiber bundle. The natural protein hydrolysate has a function to inhibit elastase. The pantetheine sulfonate or a derivative thereof and the glycyrrhetinic acid or a derivative thereof each has a function of suppressing an inflammatory factor. The hydroquinone or a glycoside thereof, esculin, esculetin, glabridin, methoxysalicylic acid, tranexamic acid or a derivative thereof, and ascorbic acid or a derivative thereof each have a function to eliminate active oxygen so that oxidation stress on the dermis is suppressed. The content of those active ingredient in the vesicle of the present invention may be set an enough amount so that the above-mentioned functions are exhibited, and for example, the content of each of the active ingredient may be preferably 0.1 to 30 mass % and more preferably 1 to 10 mass % with respect to the total amount of the vesicle.

The vesicle of the present invention can contain an arbitrary ingredient generally used in the vesicle and the external preparation for skin in addition to the above-mentioned essential ingredients and preferred ingredients. Such appropriate compounds may preferably include polyvalent alcohols such as glycerin, diglycerin, dipropylene glycol, 1,3-butanediol, 1,2-pentanediol, isoprene glycol, 1,2-hexanediol, 1,2-octanediol, and polyethylene glycol; cyclic alcohols such as cholesterol, campesterol, sitosterol, and stigmasterol; phospholipids such as lecithin, hydrogenated lecithin, hydroxylated lecithin, phosphatidyl ethanolamine, phosphatidyl inositol, phosphatidyl serine, and phosphatidyl glycerol; fatty acids such as oleic acid, capric acid, caprylic acid, and stearic acid; higher alcohols such as cetanol, stearyl alcohol, and oleyl alcohol; methylparaben; and ethylparaben. Of those, particularly preferred examples include cyclic alcohols, in particular, plant sterols (phytosterol) such as campesterol, sitosterol, and stigmasterol; polyvalent alcohol and even glycerine. The content of the phytosterol is preferably 2:1 to 1:2 with respect to $\alpha,\epsilon$-bis($\gamma$-N—($C_{10-30}$)acylglytamine)lysine, and the content of the polyvalent alcohol which is an essential ingredient, is preferably 5 to 15 times greater than that of $\alpha,\epsilon$-bis($\gamma$-N—($C_{10-30}$)acylglytamine) lysine. The vesicle of the present invention can be used to produce a vesicle dispersion composition by processing the essential ingredients by a general method, the preferred ingredients, and the arbitrary ingredients.

(4) External Preparation for Skin of the Present Invention

An external preparation for skin of the present invention is characterized by containing the above-mentioned vesicle. As the external preparation for skin contains the vesicle, an active ingredient is delivered to the dermis, and further, the $\alpha,\epsilon$-bis($\gamma$-N—($C_{10-30}$)acylglutamyl)lysine, which is a constituent of the vesicle, acts on the dermis to improve the property of the dermis. In order to exhibit those effects, the content of the vesicle is preferably 0.1 to 10 mass %, and more preferably 0.5 to 5 mass with respect to the total amount of the external preparation for skin. If the content is too small, enough amounts of the $\alpha,\epsilon$-bis($\gamma$-N—($C_{10-30}$)acylglutamyl) lysine, the ceramides, and the active ingredients may not reach to the dermis for exhibiting the effects, whereas if the content is too large, the effect level reaches to a limit, thereby impairing a degree of freedom for formulation.

The external preparation for skin of the present invention can be applied without any specific limitation as long as it is externally applicable to the skin in general. Preferred examples of the external preparation include cosmetics containing quasi-drugs, dermal medicines for external application, and externally applicable dermatological sundries. Of those, cosmetics are particularly preferable. This is because in the cosmetics, dermal access is desired, and many active ingredients with low dermal access are contained therein. Preferred examples of the cosmetics include lotion cosmetics, milky lotion cosmetics, essence cosmetics, cream cosmetics, pack cosmetics, cosmetic removers, and cleansing cosmetics. Further, as dosage forms thereof, cosmetics are not particularly limited as long as being generally known in the field of cosmetics, and may be preferably applied to lotion formulations, oil-in-water emulsion formulations, water-in-oil emulsion formulations, composite emulsion emulsifying formulations, and the like.

The external preparation for skin of the present invention can contain optional ingredients used commonly in an external preparation for skin as well as those essential ingredients. Preferred examples of such optional ingredients include: oils/waxes such as *macadamia* nut oil, avocado oil, corn oil, olive oil, rapeseed oil, sesame oil, castor oil, safflower oil, cottonseed oil, jojoba oil, coconut oil, palm oil, liquid lanolin, cured coconut oil, cured oil, Japan wax, cured castor oil, beeswax, candelilla wax, carnauba wax, ibota wax, lanolin, reduced lanolin, hard lanolin, and jojoba wax; hydrocarbons such as liquid paraffin, squalane, pristane, ozokerite, paraffin, ceresin, vaseline, and microcrystalline wax; higher fatty acids such as oleic acid, isostearic acid, lauric acid, myristic acid, palmitic acid, stearic acid, behenic acid, and undecylenic acid; higher alcohols such as cetyl alcohol, stearyl alcohol, isostearyl alcohol, behenyl alcohol, octyldodecanol, myristyl alcohol, and cetostearyl alcohol; synthetic ester oils such as cetyl isooctanoate, isopropyl myristate, hexyldecyl isostearate, diisopropyl adipate, di-2-ethylhexyl sebacate, cetyl lactate, diisostearyl malate, ethylene glycol di-2-ethyl hexanoate, neopentylglycol dicaprate, glyceryl di-2-heptylundecanoate, glyceryl tri-2-ethylhexanoate, trimethylolpropane tri-2-ethylhexanoate, trimethylolpropane triisostearate, and pentane erythrite tetra-2-ethylhexanoate; chain polysiloxanes such as dimethylpolysiloxane, methylphenylpolysiloxane, and diphenylpolysiloxane; cyclic polysiloxanes such as octamethylcyclotetrasiloxane, decamethylcyclopentasiloxane, and dodecamethyl cyclohexanesiloxane; modified polysiloxanes such as amino-modified polysiloxane, polyether-modified polysiloxane, alkyl-modified polysiloxane, and fluorine-modified polysiloxane; oil agents such as silicone oil; anionic surfactants such as fatty acid soaps (such as sodium laurate and sodium palmitate), potassium laurylsulfate, and triethanolamine alkylsulfate ether; cationic surfactants such as trimethyl ammonium stearyl chloride, benzalkonium chloride, and laurylamine oxide; amphoteric surfactants such as imidazoline-based amphoteric surfactants (such as a 2-cocoyl-2-imidazolinium hydroxide-1-carboxyethyloxy disodium salt), betaine-based surfactants (such as alkyl betaine, amide betaine, and sulfo betaine), and acylmethyl taurine; nonionic surfactants such as sorbitan fatty acid esters (such as sorbitan monostearate and sorbitan sesquioleate), glycerin fatty acid esters (such as glycerin monostearate), propyleneglycol fatty acid esters (such as propyleneglycol monostearate), cured castor oil derivatives, glycerol alkyl ether, POE sorbitan fatty acid esters (such as POE sorbitan monooleate and polyoxyethylene sorbitan monostearate), POE sorbitol fatty acid esters (such as POE-sorbitol monolaurate), POE glycerol fatty acid esters (such as POE-glycerin monoisostearate), POE fatty acid esters (such as polyethyleneglycol monooleate and POE distearate), POE alkyl ethers (such as POE2-octyldodecyl ether), POE alkylphenyl ethers (such as POE nonylphenyl ether), pluronic types, POE/POP alkyl ethers (such as POE/POP2-decyltetradecyl ether), tetronic types, POE castor oil/cured castor oil derivatives (such as POE castor oil and POE cured castor oil), sucrose fatty acid ester, and alkyl glycoside; polyvalent alcohols such as polyethylene glycol, glycerin, 1,3-butylene glycol, erythritol, sorbitol, xylitol, maltitol, propylene glycol, dipropylene glycol, diglycerin, isoprene glycol, 1,2-pentanediol, 2,4-hexanediol, 1,2-hexanediol, and 1,2-octanediol; moisture ingredients such as sodium pyrrolidone carboxylate, lactate, and sodium lactate; fine particles such as mica, talc, kaolin, synthetic mica, calcium carbonate, magnesium carbonate, silicic anhydride (silica), aluminum oxide, and barium sulfate, whose surfaces may be treated; inorganic pigments such as red iron oxide, yellow iron oxide, black iron oxide, cobalt oxide, ultramarine blue, iron blue, titanium oxide, and zinc oxide, whose surfaces may be treated; pearl agents such as mica titanium, fish scale foil, and bismuth oxychloride, whose surfaces may be treated; organic dyes such as Red No. 202, Red No. 228, Red No. 226, Yellow No. 4, Blue No. 404, Yellow No. 5, Red No. 505, Red No. 230, Red No. 223, Orange No. 201, Red No. 213, Yellow No. 204, Yellow No. 203, Blue No. 1, Green No. 201, Purple No. 201, and Red No. 204, which may be laked; organic fine particles such as polyethylene powder, polymethyl methacrylate, nylon powder, and organopolysiloxane elastomer; p-aminobenzoate-based ultraviolet absorbent; an anthranilate-based ultraviolet absorbent; a salicylate-based ultraviolet absorbent; a cinnamate-based ultraviolet absorbent; a benzophenone-based ultraviolet absorbent; a sugar-based ultraviolet absorbent; ultraviolet absorbents such as 2-(2'-hydroxy-5'-t-octylphenyl) benzotriazole, and 4-methoxy-4'-t-butyldibenzoylmethane; lower alcohols such as ethanol and isopropanol; vitamins such as vitamin A or derivatives thereof; vitamin B types such as vitamin $B_6$ hydrochloride, vitamin $B_6$ tripalmitate, vitamin $B_6$ dioctanoate, vitamin $B_2$ or derivatives thereof, vitamin $B_{12}$, and vitamin $B_{15}$ or derivatives thereof; vitamin E types such as α-tocopherol, β-tocopherol, γ-tocopherol, and vitamin E acetate, vitamin D types, vitamin H, pantothenic acid, pantethine, and pyrroloquinoline quinone; and antibacterial agents such as phenoxyethanol.

The external preparation for skin of the present invention can be produced by processing the essential ingredient and the optional ingredient by a conventional method.

Hereinafter, the present invention is described in more detail by way of examples, but it is needless to say that the present invention is not limited to those examples.

Example 1

Vesicle dispersion liquid 1 of the present invention was produced according to the following formulation. That is, ingredients A and ingredients B were each heated to 70° C. to be homogeneously dissolved, and the ingredients B were gradually added to the ingredients A while stirring, to thereby obtain a vesicle dispersion liquid. A part of the vesicle dispersion liquid was separated and weighed, and thereafter, centrifuged, the supernatant was removed, the resultant was washed twice with water, the moisture thereof was removed by drying, and the resultant was weighed, to thereby calculate the content mass of the vesicle in the vesicle dispersion liquid, which was found to be 9.3 mass %. Further, in the same procedure, the following were treated in the same manner: Comparative Example 1 in which lecithin was substituted for "Pellicer L-30"; Comparative Example 2 in which "Pellicer L-30" was substituted for "Ceramide TIC-001"; and Comparative Example 3 in which polyoxyethylene (2) oleate was substituted for diglycerin monooleate. As a result of observation using a polarization microscope, polarized light was not recognized in any of Comparative Example 1, Comparative Example 2, and Comparative Example 3, and hence, it was found that Comparative Example 1, Comparative Example 2, and Comparative Example 3 did not form vesicle disperse system.

TABLE 1

| Ingredients | Mass % |
|---|---|
| A | |
| "Ceramide TIC-001" | 1 |
| Sitosterol | 1 |
| "Pellicer L-30" | 1 |
| Diglycerin monooleate | 3 |
| Glycerin | 10 |
| B | |
| Phenoxyethanol | 0.5 |
| Water | 83.5 |
| Total | 100 |

Example 2

Reference Example 1

A whole plant of Palmaria palmate was dried, and thereafter weighed 100 g from the dried product. 2 L of water were added thereto, the resultant was gradually heated up to 60° C., the temperature was maintained for 3 hours, and then the resultant was left standing to cool to room temperature. After being cooled, insolubles were removed by filtration, and the filtrate was freeze dried to thereby obtain Palmaria extract 1.

The above-mentioned Palmaria extract 1 was used to produce Vesicle dispersion liquid 2 in the same manner as in Example 1. Further, in the same manner as in Example 1, the following were treated in the same manner: Comparative Example 4 in which lecithin was substituted for "Pellicer L-30"; Comparative Example 5 in which "Pellicer L-30" was substituted for "Ceramide TIC-001"; and Comparative Example 6 in which polyoxyethylene (2) oleate was substituted for diglycerin monooleate. As a result of observation using a polarization microscope, polarized light was not recognized in any of Comparative Example 4, Comparative Example 5, and Comparative Example 6, and hence, it was found that Comparative Example 4, Comparative Example 5, and Comparative Example 6 did not form vesicle disperse system. Further, the mass of the vesicle contained in Vesicle dispersion liquid 2 was 9.8 mass %.

TABLE 2

| Ingredients | Mass % |
|---|---|
| A | |
| "Ceramide TIC-001" | 1 |
| Sitosterol | 1 |
| "Pellicer L-30" | 1 |
| Diglycerin monooleate | 3 |
| 10% aqueous solution of Palmaria extract 1 | 1 |
| Glycerin | 10 |
| B | |
| Phenoxyethanol | 0.5 |
| Water | 82.5 |
| Total | 100 |

Test Example 1

Vesicle dispersion liquid 1, Vesicle dispersion liquid 2, Comparative Example 4, Comparative Example 5, and Comparative Example 6 were each used as a sample. The skin was previously applied and blocked with 1% sodium lauryl sulfate aqueous solution for 24 hours to enhance transepidermal water loss (TEWL), and was applied and blocked with the sample for 6 hours, and 30 minutes after removing a bandage, TEWL was determined using Tewameter (manufactured by Integral Corporation). It should be noted that water was applied as a control. Table 3 shows the results. It is found that further excellent TEWL-suppressing effect is recognized in the vesicle disperse system. This is inferably because the dermis-reaching property of Palmaria extract 1, which is an active ingredient, has been enhanced owing to the vesicle. Further, it was recognized that "Pellicer L-30" itself had a function of suppressing TEWL.

TABLE 3

| Samples | TEWL |
|---|---|
| Control | 28 |
| Vesicle dispersion liquid 1 | 21 |
| Vesicle dispersion liquid 2 | 13 |
| Comparative Example 4 | 24 |
| Comparative Example 5 | 18 |
| Comparative Example 6 | 19 |

Example 3

Reference Example 2

To 500 g of chopped pieces of the rhizome of *Coptis japonica* belonging *Coptis* (Ranunculaceae), 3 L of 50% ethanol aqueous solution were added, the mixture was heated under stirring and was refluxed for 3 hours. After being cooled to room temperature, insolubles were removed by filtration. The resultant was subjected to vacuum concentration, and 1 L of water and 1 L of ethyl acetate were added to the residue to perform liquid-liquid extraction. The ethyl acetate layer was separated, and the layer was washed twice with 500 mL of water followed by drying with anhydrous sodium sulfate. After that, the resultant was subjected to vacuum concentration to remove the solvent, to thereby obtain *Coptis japonica* extract 1.

Reference Example 3

The same treatment was performed except that the fruit skin of *Citrus aurantium* (Rutaceae) was used instead of the rhizome of *Coptis japonica* belonging to *Coptis* (Ranunculaceae), to thereby obtain *Citrus aurantium* extract 1.

Reference Example 4

The same treatment was performed except that the aerial part of *Houttuynia cordata* (Saururaceae) was used instead of the rhizome of *Coptis japonica* belonging to *Coptis* (Ranunculaceae), to thereby obtain *Houttuynia cordata* extract 1.

Reference Example 5

The same treatment was performed except that the leaf of *Rosmarinus officinalis* (Lamiaceae) was used instead of the rhizome of *Coptis japonica* belonging to *Coptis* (Ranunculaceae), to thereby obtain *Rosmarinus officinalis* extract 1.

Reference Example 6

The same treatment was performed except that the tree bark of *Betula alba* (Betulaceae) was used instead of the rhizome of *Coptis japonica* belonging to t *Coptis* (Ranunculaceae), to thereby obtain *Betula alba* extract 1.

Reference Example 7

The same treatment was performed except that the aerial part of *Achillea millefolium* (Compositae) was used instead of the rhizome of *Coptis japonica* belonging to *Coptis* (Ranunculaceae), to thereby obtain *Achillea millefolium* extract 1.

Reference Example 8

The same treatment was performed except that the aerial part of *Centella asiatica* (Apiaceae) was used instead of the rhizome of *Coptis japonica* belonging to *Coptis* (Ranunculaceae), to thereby obtain *Centella asiatica* extract 1.

Reference Example 9

The same treatment was performed except that the leaf of *Engelhardtia chrysolepis* (Juglandaceae) was used instead of the rhizome of *Coptis japonica* belonging to *Coptis* (Ranunculaceae), to thereby obtain *Engelhardtia chrysolepis* extract 1.

Reference Example 10

The same treatment was performed except that the rhizome of *Ophiopogon japonicus* (Liliaceae) was used instead of the rhizome of *Coptis japonica* belonging to *Coptis* (Ranunculaceae), and that the 50% ethanol aqueous solution was used instead of the ethanor, to thereby obtain *Ophiopogon japonicus* extract 1.

A vesicle dispersion liquid in which the vesicle of the present invention was dispersed was obtained in the same manner as in Example 2 according to the following formulation.

TABLE 4

| Ingredients | Mass % |
| --- | --- |
| A | |
| "Ceramide TIC-001" | 1 |
| Sitosterol | 1 |
| "Pellicer L-30" | 1 |
| Diglycerin monooleate | 3 |
| Ingredients shown in Table 5 | 0.1 |
| Glycerin | 10 |
| B | |
| Phenoxyethanol | 0.5 |
| Water | 83.4 |
| Total | 100 |

TABLE 5

| Vesicle dispersion liquids | Ingredients | Property |
| --- | --- | --- |
| 3 | *Coptis japonica* extract 1 | Vesicle disperse system |
| 4 | *Citrus aurantium* extract 1 | Vesicle disperse system |
| 5 | *Houttuynia cordata* extract 1 | Vesicle disperse system |
| 6 | *Rosmarinus officinalis* extract 1 | Vesicle disperse system |
| 7 | *Betula alba* extract 1 | Vesicle disperse system |
| 8 | *Achillea millefolium* extract 1 | Vesicle disperse system |
| 9 | *Centella asiatica* extract 1 | Vesicle disperse system |
| 10 | *Engelhardtia chrysolepis* extract 1 | Vesicle disperse system |
| 11 | *Ophiopogon japonicus* extract 1 | Vesicle disperse system |
| 12 | Eugenol | Vesicle disperse system |
| 13 | Oleanolic acid | Vesicle disperse system |
| 14 | Oleanolic acid methyl ester | Vesicle disperse system |
| 15 | Ascorbic acid glycoside | Vesicle disperse system |
| 16 | Soybean protein hydrolysate | Vesicle disperse system |
| 17 | Lauroyl silk protein hydrolysate | Vesicle disperse system |
| 18 | Arbutin | Vesicle disperse system |
| 19 | Pantetheine sulfonate | Vesicle disperse system |
| 20 | Glabridin | Vesicle disperse system |
| 21 | Esculetin | Vesicle disperse system |
| 22 | Stearyl glycyrrhetinate | Vesicle disperse system |

Example 4

The same studies were conducted by using various surfactants in the same manner as in Example 3.

TABLE 6

| Ingredients | Mass % |
| --- | --- |
| A | |
| "Ceramide TIC-001" | 1 |
| Sitosterol | 1 |
| "Pellicer L-30" | 1 |
| Surfactants shown in Table 7 | 3 |
| 10% aqueous solution of *Palmaria* extract 1 | 1 |
| Glycerin | 10 |
| B | |
| Phenoxyethanol | 0.5 |
| Water | 82.5 |
| Total | 100 |

TABLE 7

| Vesicle dispersion liquids | Ingredients | Property |
| --- | --- | --- |
| 23 | Diglycerin monostearate | Vesicle disperse system |
| 24 | Diglycerin monoisostearate | Vesicle disperse system |
| 25 | Triglycerin diisostearate | Vesicle disperse system |
| 26 | Pentaglycerin trioleate | Vesicle disperse system |
| 27 | Decaglycerin hexaoleate | Vesicle disperse system |
| 28 | pyroglutamic acid glycerin oleic acid | Vesicle disperse system |

Example 5

Vesicle dispersion liquid 29 was produced in the same manner as in Example 3 according to the following formulation. An emulsified state was also observed in a part of the vesicles.

TABLE 8

| Ingredients | Mass % |
| --- | --- |
| A | |
| "Ceramide TIC-001" | 1 |
| Sitosterol | 1 |

TABLE 8-continued

| Ingredients | Mass % |
|---|---|
| "Pellicer L-30" | 1 |
| Decaglycerin monostearate | 3 |
| 10% aqueous solution of *Palmaria* extract 1 | 1 |
| Glycerin | 10 |
| B | |
| Phenoxyethanol | 0.5 |
| Water | 82.5 |
| Total | 100 |

Example 6

Vesicle dispersion liquid 30 was produced in the same manner as in Example 3 according to the following formulation. It was a vesicle disperse system.

TABLE 9

| Ingredients | Mass % |
|---|---|
| A | |
| "Ceramide TIC-001" | 0.3 |
| Sitosterol | 0.3 |
| "Pellicer L-30" | 1 |
| Decaglycerin monostearate | 3 |
| 10% aqueous solution of *Palmaria* extract 1 | 1 |
| 1,3-butanediol | 10 |
| B | |
| Phenoxyethanol | 0.5 |
| Water | 83.9 |
| Total | 100 |

Example 7

The same studies were conducted by using different kinds of ceramides in the same manner as in Example 3.

TABLE 10

| Ingredients | Mass % |
|---|---|
| A | |
| Ingredients shown in Table 11 | 1 |
| Sitosterol | 1 |
| "Pellicer L-30" | 1 |
| Decaglycerin monostearate | 3 |
| 10% aqueous solution of *Palmaria* extract 1 | 1 |
| Glycerin | 10 |
| B | |
| Phenoxyethanol | 0.5 |
| Water | 82.5 |
| Total | 100 |

TABLE 11

| Vesicle dispersion liquids | Ingredients | Property |
|---|---|---|
| 31 | "Ceramide I" | Vesicle disperse system |
| 32 | "Ceramide III" | Vesicle disperse system |
| 33 | "Ceramide IIIA" | Vesicle disperse system |
| 34 | "Ceramide IIIB" | Vesicle disperse system |
| 35 | "Ceramide IV" | Vesicle disperse system |

Example 8

A milky liquid was produced, which is the external preparation for skin, according to the following formulation. That is, each of ingredients (A) was mixed with each other and the mixture was heated to 80° C. On the other hand, each of ingredients (B) was heated to 80° C. The mixture of the ingredients (B) was added to the mixture of the ingredients (A), and was stirred to be emulsified. Still further, ingredients (C) were added thereto to neutralize the mixture, and after that, the mixture was stirred and cooled to 35° C., to thereby produce the milky liquids. Any of the milky liquids maintained the vesicle disperse system after storage for one month at 5° C., 20° C., or 40° C.

TABLE 12

| Ingredients | Mass % |
|---|---|
| (A) | |
| Behenyl alcohol | 0.5 |
| Cetyl isooctanoate | 2.0 |
| Squalane | 8.0 |
| Dimethicone | 2.0 |
| Sorbitan sesquistearate | 1.5 |
| POE (45) stearic acid | 1.0 |
| Cetyl stearate | 0.5 |
| Behenic acid | 0.5 |
| (B) | |
| 1,3-butanediol | 5.0 |
| Glycerin | 5.0 |
| 1,2-octanediol | 1.0 |
| Pure water | 35.5 |
| Ingredients shown in Table 13 | 15 |
| Dipotassium glycyrrhizinate | 0.1 |
| (C) | |
| Pure water | 21.8 |
| Potassium hydroxide | 0.6 |
| Total | 100 |

TABLE 13

| Samples | Ingredients |
|---|---|
| Milky liquid 1 | Vesicle dispersion liquid 1 |
| Milky liquid 2 | Vesicle dispersion liquid 2 |
| Milky liquid 3 | Vesicle dispersion liquid 3 |
| Milky liquid 4 | Vesicle dispersion liquid 4 |
| Milky liquid 5 | Vesicle dispersion liquid 5 |
| Milky liquid 6 | Vesicle dispersion liquid 6 |
| Milky liquid 7 | Vesicle dispersion liquid 7 |
| Milky liquid 8 | Vesicle dispersion liquid 8 |
| Milky liquid 9 | Vesicle dispersion liquid 9 |
| Milky liquid 10 | Vesicle dispersion liquid 10 |
| Milky liquid 11 | Vesicle dispersion liquid 11 |
| Milky liquid 12 | Vesicle dispersion liquid 12 |
| Milky liquid 13 | Vesicle dispersion liquid 13 |
| Milky liquid 14 | Vesicle dispersion liquid 14 |
| Milky liquid 15 | Vesicle dispersion liquid 15 |
| Milky liquid 16 | Vesicle dispersion liquid 16 |

TABLE 13-continued

| Samples | Ingredients |
| --- | --- |
| Milky liquid 17 | Vesicle dispersion liquid 17 |
| Milky liquid 18 | Vesicle dispersion liquid 18 |
| Milky liquid 19 | Vesicle dispersion liquid 19 |
| Milky liquid 20 | Vesicle dispersion liquid 20 |
| Milky liquid 21 | Vesicle dispersion liquid 21 |
| Milky liquid 22 | Vesicle dispersion liquid 22 |
| Milky liquid 23 | Vesicle dispersion liquid 23 |
| Milky liquid 24 | Vesicle dispersion liquid 24 |
| Milky liquid 25 | Vesicle dispersion liquid 25 |
| Milky liquid 26 | Vesicle dispersion liquid 26 |
| Milky liquid 27 | Vesicle dispersion liquid 27 |
| Milky liquid 28 | Vesicle dispersion liquid 28 |
| Milky liquid 29 | Vesicle dispersion liquid 29 |
| Milky liquid 30 | Vesicle dispersion liquid 30 |
| Milky liquid 31 | Vesicle dispersion liquid 31 |
| Milky liquid 32 | Vesicle dispersion liquid 32 |
| Milky liquid 33 | Vesicle dispersion liquid 33 |
| Milky liquid 34 | Vesicle dispersion liquid 34 |
| Milky liquid 35 | Vesicle dispersion liquid 35 |

INDUSTRIAL APPLICABILITY

According to the present invention, there may be provided a technique for allowing an active ingredient for improving or maintaining a dermal environment to reach the dermis.

The present invention may be applied to an external preparation for skin.

What is claimed is:

1. A vesicle comprising:
   1) an $\alpha,\epsilon$-bis ($\gamma$-N—($C_{10-30}$)acylglutamyl)lysine and/or a salt thereof;
   2) a ceramide and/or a derivative thereof; and
   3) one or more selected from a glycerin fatty acid ester, a polyglycerin fatty acid ester, and a pyroglutamic acid glycerin fatty acid ester.

2. A vesicle according to claim 1, wherein an acyl group in the $\alpha,\epsilon$-bis ($\gamma$-N—($C_{10-30}$)acylglutamyl)lysine is a lauroyl group.

3. A vesicle according to claim 1, wherein the ceramide or the derivative thereof is a ceramide type 2 or a ceramide type 3.

4. A vesicle according to claim 1, wherein the one or more selected from a glycerin fatty acid ester, a polyglycerin fatty acid ester, and a pyroglutamic acid glycerin fatty acid ester are one or more selected from diglycerin monooleate, diglycerin monoisostearate, decaglycerin monooleate, decaglycerin monoisostearate, decaglycerin pentaoleate, and decaglycerin pentaisostearate.

5. A vesicle according to claim 1, further comprising one or more of the following active ingredients for improving or maintaining a dermal environment: an extract of *Coptis*; an extract of *Citrus aurantium*; an extract of red algae; an extract of *Houttuynia*; an extract of *Rosmarinus officinalis*; an extract of *Betula alba*; an extract of *Achillea*; an extract of *Syzygium aromaticum*; an extract of *Hypericum*; an extract of *Centella*; an extract of *Engelhardtia chrysolepis*; an extract of *Ophiopogon*; a natural protein hydrolysate or an acylated product thereof; oleanolic acid or oleanolic acid methyl ester; betuline; betulinic acid; pantetheine sulfonate; glycyrrhetinic acid or stearyl glycrrhetinate; hydroquinone or a glycoside thereof; esculin; esculetin; glabridin; methoxysalicylic acid; tranexamic acid; ascorbic acid or a glycoside thereof; and L-carnitine.

6. An external preparation for skin, comprising the vesicle according to any one of claims 1 to 5.

7. A method for delivering an active agent to the dermis layer of skin comprising administering a composition comprising vesicles according to claim 1 and the active agent to the skin of an individual in need thereof.

8. The method according to claim 7, wherein an acyl group in the $\alpha,\epsilon$-bis($\gamma$-N—($C_{10-30}$)acylglutamyl)lysine is a lauroyl group.

9. The method according to claim 7, wherein the ceramide or the derivative thereof is a ceramide type 2 or a ceramide type 3.

10. The method according to claim 7, wherein the one or more selected from a glycerin fatty acid ester, a polyglycerin fatty acid ester, and a pyroglutamic acid glycerin fatty acid ester are one or more selected from diglycerin monooleate, diglycerin monoisostearate, decaglycerin monooleate, decaglycerin monoisostearate, decaglycerin pentaoleate, and decaglycerin pentaisostearate.

11. The method according to claim 7, wherein the active ingredient is selected from the group consisting of an extract of *Coptis*; an extract of *Citrus aurantium*; an extract of red algae; an extract of *Houttuynia*; an extract of *Rosmarinus officinalis*; an extract of *Betula alba*; an extract of *Achillea*; an extract of *Syzygium aromaticum*; an extract of *Hypericum*; an extract of *Centella*; an extract of *Engelhardtia chrysolepis*; an extract of *Ophiopogon*; a natural protein hydrolysate or an acylated product thereof; oleanolic acid or oleanolic acid methyl ester; betuline; betulinic acid; pantetheine sulfonate; glycyrrhetinic acid or stearyl glycrrhetinate; hydroquinone or a glycoside thereof; esculin; esculetin; glabridin; methoxysalicylic acid; tranexamic acid; ascorbic acid or a glycoside thereof; and L-carnitine.

* * * * *

UNITED STATES PATENT AND TRADEMARK OFFICE
CERTIFICATE OF CORRECTION

PATENT NO. : 8,865,208 B2
APPLICATION NO. : 12/601481
DATED : October 21, 2014
INVENTOR(S) : Hidetaka Akatsuka et al.

Page 1 of 1

It is certified that error appears in the above-identified patent and that said Letters Patent is hereby corrected as shown below:

In The Specification

In column 2 at line 5, Change "(ε-" to --(γ- --.

In column 8 at line 11, Change "amyristic" to --a myristic--.

In column 9 at line 33, Change "Hypericumperforatum," to --Hypericum perforatum,--.

In column 9 at line 34, Change "chrisolepis" to --chrysolepis--.

In column 10 at lines 26-27, Change "acylglytamine)" to --acylglutamine)--.

In column 10 at line 29, Change "acylglytamine)" to --acylglutamine)--.

In column 11 at line 12, Change "ibota wax," to --ibotta wax,--.

In column 11 at lines 31-32, Change "dodecamethyl cyclohexanesiloxane;" to --dodecamethylcyclohexanesiloxane;--.

In column 15 at line 31 (approx.), Change "ethanor," to --ethanol,--.

In The Claims

In column 20 at line 12, In Claim 5, change "glycrrhetinate;" to --glycyrrhetinate;--.

In column 20 at line 45, In Claim 11, change "glycrrhetinate;" to --glycyrrhetinate;--.

Signed and Sealed this
Thirtieth Day of June, 2015

Michelle K. Lee
*Director of the United States Patent and Trademark Office*